United States Patent [19]

Romesser et al.

[11] Patent Number: 5,295,985
[45] Date of Patent: Mar. 22, 1994

[54] POLYESTERS AND THEIR USE IN COMPOSTABLE PRODUCTS SUCH AS DISPOSABLE DIAPERS

[75] Inventors: James A. Romesser; Hyunkook Shin; Raymond F. Tietz, all of Wilmington, Del.

[73] Assignee: E. I. Du Pont de Nemours and Company, Wilmington, Del.

[21] Appl. No.: 973,240

[22] Filed: Nov. 6, 1992

Related U.S. Application Data

[63] Continuation of Ser. No. 834,797, Feb. 13, 1992, abandoned, which is a continuation-in-part of Ser. No. 769,414, Oct. 1, 1991, abandoned, and a continuation-in-part of Ser. No. 769,417, Oct. 1, 1991, abandoned, and a continuation-in-part of Ser. No. 771,019, Oct. 1, 1991, and a continuation-in-part of Ser. No. 645,995, Jan. 25, 1991, Pat. No. 5,097,005, and a continuation-in-part of Ser. No. 645,849, Jan. 25, 1991, Pat. No. 5,097,004, which is a continuation of Ser. No. 522,134, May 11, 1990, Pat. No. 5,053,482.

[51] Int. Cl.$^5$ ............................................. A61F 13/15
[52] U.S. Cl. .................................... 604/358; 528/272; 528/295; 528/301; 528/302; 528/308.6; 525/437; 525/450; 525/471; 428/224; 428/364; 428/480; 428/481; 521/182; 604/372
[58] Field of Search .............. 528/272, 295, 301, 302, 528/308.6; 525/437, 450, 471; 428/224, 364, 480, 481; 521/182; 604/358, 372

[56] References Cited

U.S. PATENT DOCUMENTS

| | | | |
|---|---|---|---|
| 3,018,272 | 1/1962 | Griffing et al. | 528/293 |
| 3,853,820 | 12/1974 | Vachon | 528/295 |
| 4,418,116 | 11/1983 | Scott | 428/288 |
| 4,483,976 | 11/1984 | Yamamoto et al. | 528/295 |
| 4,526,738 | 7/1985 | Miyoshi et al. | 264/176 |
| 4,704,329 | 11/1987 | Hancock et al. | 428/369 |
| 4,883,706 | 11/1989 | Grosjean | 428/215 |

OTHER PUBLICATIONS

Ingamells, J. Appl. Poly. Sci., vol. 26, 4087–4101 (1981).
Grassie, "Developments in Polymer Degradation—5"", pp. 112–119, (1984), Applied Science Publishers.

*Primary Examiner*—Samuel A. Acquah

[57] ABSTRACT

The invention provides novel polyesters, fibers and films, nonwovens from the fibers and disposable products of the polyesters such as diapers. The products are degradable under the conditions typically existing in waste compositing processes, have low ingredient costs and yet provide strength and toughness properties adequate for end uses such as in disposable diapers. The polyesters are based upon polyester ingredients, such as polyethylene terephthalate, copolymerized with an alkali metal or alkaline earth metal 4-sulfophthalic acid derivative, and other ingredients, such as polyethylene ether glycols and/or non-aromatic diacids, such as adipic and glutaric acids.

16 Claims, No Drawings

POLYESTERS AND THEIR USE IN COMPOSTABLE PRODUCTS SUCH AS DISPOSABLE DIAPERS

CROSS-REFERENCE TO RELATED APPLICATIONS

This is a continuation of application Ser. No. 07/834,797, filed Feb. 13, 1992, now abandoned, which is a continuation-in-part of the following copending applications: Ser. Nos. 07/769,414 (Gallagher et al QP-4691), now abandoned, 07/769,417 (Gallagher et al QP-4850) now abandoned and 07/771,019 (Gallagher et al DP-4955) all filed Oct. 10, 1991, now abandoned; and Ser. Nos. 07/645,995 (Tietz QP-4710) and 07/645,849 (Gallagher et al QP-4690) both filed Jan. 25, 1991, and now U.S. Pat. Nos. 5,097,005 and 5,097,004, respectively; all of which are continuations-in-part of Ser. No. 07/522,134, filed May 11, 1990, now Tietz U.S. Pat. No. 5,053,482.

FIELD OF THE INVENTION

This invention relates to novel polyesters and products therefrom. The products include fibers, films, foams, coated papers, extruded nets, molded objects and nonwovens and disposable products such as diapers from such products. The products are degradable to innocuous materials under conditions used in municipal solid waste composting systems.

BACKGROUND OF THE INVENTION

The inadequate treatment of municipal solid waste which is being put in landfills and the increasing addition of nondegradable materials, including plastics, to the municipal solid waste streams are combining to reduce drastically the number of landfills available and to increase the costs of municipal solid waste disposal. While the recycling of reusable components of the waste stream is desirable in many instances, there are some products which do not readily fit into this framework, e.g. disposable personal absorbents such as diapers and sanitary napkins, garbage bags, and numerous other products. The composting of non-recyclable solid waste is a recognized and growing method of reducing solid waste volume for landfilling and/or making a useful product from the waste to improve the fertility of fields and gardens. One of the limitations to marketing such compost is the visible contamination by undegraded plastic such as film and fiber fragments.

As related in the aforesaid parent applications, which are hereby specifically incorporated herein by reference, there was a desire to achieve several objectives, as follows:

1- to provide components which are useful in disposable products and which are degraded into less contaminating forms under the conditions typically existing in waste composting processes. These conditions may involve temperatures no higher than 70 C., and averaging more nearly 55–60 C., humid conditions as high as 100% relative humidity, and exposure times which range from two weeks to more than three months.

2-to provide disposable components which will not only degrade aerobically/anaerobically in composting, but will continue to degrade in the soil or landfill. As long as water is present, they will continue to break down into low molecular weight fragments which can be ultimately biodegraded by microorganisms completely into biogas, biomass and liquid leachate, as for natural organics like wood.

3-to provide novel polyesters for making the aforementioned fibers, films, coatings and nonwoven sheets of the polyesters, and disposable diapers containing the nonwoven sheets.

4-to provide polyesters and derivative products which have low ingredient costs and yet provide strength and toughness properties adequate for end uses such as in disposable diapers.

Accordingly, U.S. Pat. No. 5,053,482 provided useful novel polyesters consisting essentially of recurring structural units of the formula

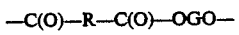

wherein R is about 97.5 to 99.9 mole % para-phenylene (abbreviation T) and about 0.1 to 2.5 mole % of an alkali metal or alkaline earth metal 5-sulfoisophthalate radical (abbreviation 5SI) and wherein G is about 60 to 80 mole % —$CH_2$—$CH_2$— (abbreviation 2G) and about 20 to 40 mole % —$(CH_2)_2$—O—$(CH_2)_2$— (abbreviation DEG), and fibers, non-woven sheet, films and combinations thereof, and disposable diapers comprising such materials. The above-mentioned U.S. Pat. Nos. 5,097,004 and 5,092,008 provided other polyesters containing 5SI radicals. U.S. Pat. Nos. 5,171,308 (QP-4691-A), 5,171,309 (DP-4955-A) and 5,219,646 (QP-4850-A), however, disclose useful compostable products are provided from additional polyesters containing sulfonate radicals other than 5SI, for example 4SP, referred to therein and hereinafter. So the object of the present invention is to provide compostable products from such copolyesters derived from 4SP.

Abbreviations and nomenclature herein, except as otherwise indicated, are as described in aforesaid U.S. Pat. No. 5,053,482, and application Ser. Nos. 07/645,849, 07/645,995, 07/769,414, 07/769,417, and 07/771,019, all of which are hereby incorporated herein by reference, as are applications QP-4560-A, QP-4690-A, QP-4691-A, QP-4710-A, QP-4850-A and DP-4955-A, being filed at the present time.

DESCRIPTION OF RELATED ART

Various polyester compositions have been suggested in the past for biodegradable end uses. These include polyhydroxybutyrate, polylactide, polycaprolactone, polyglycolide, and their copolymers. They have not been widely adopted in high volume uses, however, because they are either too expensive or their properties are inadequate for the uses mentioned above.

It is known to use salts of 5-sulfoisophthalic acid and its esters as comonomers to improve acid dyeability of polyethylene terephthalate fibers, see for example U.S. Pat. No. 3,018,272 (Griffing et al.). Moreover, this type of fiber is known to have an increased rate of hydrolytic degradation, see for example J. Appl. Poly. Sci., vol. 26, 4087–4094 (W. Ingamells et al.) and Developments in Polymer Degradation 5, edited by N. Grassie, Applied Science Publishers, 1984, pages 112–119. The use of 5-sulfoisophthalate salts together with other neutral comonomers has been disclosed to increase dye rates, but the proportion of the neutral comonomer is usually minimized to affect physical properties as little as possible, see for example U.S. Pat. Nos. 4,704,329 (Hancock et al.) and 3,853,820 (Vachon).

It is also known to use as much as 20 to 45 mole % diethylene glycol as a comonomer with ethylene glycol and terephthalic to provide polyesters having suitable melting and bonding characteristics for a nonwoven binder fiber, see for example U.S. Pat. No. 4,418,116 (Scott). Further, it is known to prepare water dispersible papermaking binder fibers which are made containing 5 to 20 mole % of diethylene glycol and preferably more than 3 mole % 5-sulfoisophthalate, see for example U.S. Pat. No. 4,483,976 (Yamamoto et al.). In the latter patent each of the specific polymers disclosed contain 7 mole % or more of the 5-sulfoisophthalate salt.

SUMMARY OF THE INVENTION

In one embodiment of the invention there is, accordingly, provided a novel fiber and film forming polyester consisting essentially of recurring structural units of the Formulae:

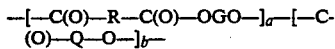

wherein about 0.1 to about 2.5 mole % of R is 4SP, an alkali metal or alkaline earth metal salt of a 4-sulfophthalic radical, up to about 40 mole % of R is a radical D selected from the group consisting of a chemical bond and one or more divalent, non-aromatic, $C_1$-$C_{10}$ hydrocarbylene radicals, and the remainder of R is a divalent aromatic radical, with at least about 85 mole % of said remainder being p-phenylene (T), wherein G is up to about 30 mole % of a polyethylene ether radical E selected from the group consisting of DEG and TEG, —$(CH_2)_2$—O—$(CH_2)_2$— and
—$(CH_2)_2$—O—$(CH_2)_2$—O—$(CH_2)_2$—, and the remainder of G is selected from the group consisting of a radical F, being a polyalkylene ether of molecular weight at least about 250, and of hydrocarbylene radicals —$(CH_2)_2$— (i.e., 2G), —$(CH_2)_3$— (i.e., 3G) and —$(CH_2)_4$— (i.e., 4G), and wherein the structural units of the formula:

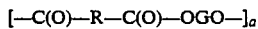

contain amounts of radicals D and/or E and/or F that are at least S, wherein S is the total of d+e+f, wherein d is the mole % of radical D, e is one quarter of the mole % of radical E, and f is the mole % of radical F, and wherein S is at least 5 mole %, wherein Q is derived from an hydroxy acid of formula

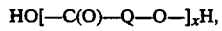

where x is an integer, such hydroxy acid having a melting point at least 5 C below its decomposition temperature, and Q is selected from the group consisting of a chemical bond and hydrocarbylene radicals —$(CH_2)_n$—, where n is an integer from 1 to 5, —C(R')H—, and —C(R')HCH$_2$—, wherein R' is selected from the group of —CH$_3$ and —CH$_2$CH$_3$, and wherein "a" and "b" are mole fractions of the polymer, and the mole fraction "a" may be 0.6 to 1 and, correspondingly, mole fraction "b" may be 0 to 0.4.

Other embodiments of the invention include fibers, foams, films and coatings of the above polyesters and nonwovens of the fibers. The invention also contemplates disposable products, such as diapers, which contain an absorbent body portion, with, on at least one surface, a water permeable nonwoven sheet composed of the polyester fibers, a water impermeable film of the polyester, or a combination thereof.

It is a finding of the invention that the above polyesters, derived for example from terephthalic acid (abbreviation T), a metal salt of a 4-sulfophthalic acid (abbreviation 4SP), ethylene glycol (abbreviation 2G) and diethylene glycol (abbreviation DEG), undergo degradation when subjected to the conditions of high humidity and temperature that typically characterize composting operations.

It is significant that the bulk of the monomers resulting from degradation, i.e. the terephthalic acid and the glycols, are readily digested by organisms in solid waste or compost to create carbon dioxide, and water. It is especially significant that the sulfo-constituent (4SP) is readily digested in at least one medium, as shown hereafter in Example 3.

Many copolyesters which may be made by copolymerization with 4-sulfophthalic acid (4SP) will hydrolyze readily. Not all such copolymers are acceptable in the end uses contemplated. The polymers should exhibit the desired physical properties, and be processable under practical conditions, but the products of hydrolysis should desirably have the potential to be digested by the organisms likely to be found in waste disposal facilities and compost. This cannot be achieved by all monomers used in preparing other copolyesters. We have found, for example, that terephthalic acid is decomposed substantially completely in such a test over 28 days, and that ethylene glycol and polyethylene glycol (with MW 250 and 3500) are also satisfactorily digested by organisms typical of those found in waste disposal systems; typically, as the molecular weight increases, degradation generally becomes slower. Non-aromatic acids (such as adipic acid and glutaric acid) are known to be decomposed rapidly, and carbonic acid gives carbon dioxide and water directly. It may well be that the ability of sodium 4-sulfophthalate radicals to decompose readily under the test conditions indicated may prove advantageous over other sulfonated ingredients. Sodium dimethyl 5-sulfoisophthalate, for example, has shown slower degradation in some tests. In this regard, it should be recognised that the rate and extent of decomposition is affected significantly by selection of particular organisms and other specifics during composting.

A preferred polyester of the invention is that indicated by the abbreviation 2G-T/6/4SP(78.4/20/1.6), where the numbers connote the mole percentages of the various diacid monomeric units in the polyester. Such abbreviations to connote compositions on a mole % basis will be used throughout this specification.

These polyesters provide useful materials having applications in end uses where containment of body fluids is necessary and disposability is desirable, e.g., in a degradable film or in a fabric or paper coated with a film which will conform easily to body contours yet act as an effective barrier to penetration of body fluids. It is especially preferred that such films or coated sheets should have a reduced tendency to rattle and rustle when flexed during body movements. Such a film or coated sheet must have adequate strength and toughness to allow its survival during use. In order that it not leave objectionable residues when disposed of, it should disintegrate quickly when placed in proper waste disposal facilities and, ultimately, degrade substantially completely to innocuous materials, such as carbon dioxide, methane and water.

DETAILED DESCRIPTION OF PREFERRED EMBODIMENTS

The polyesters of the invention consist essentially of recurring structural units of the Formulae:

—[—C(O)—R—C(O)—OGO—]$_a$—[—C(O)—Q—O—]$_b$— wherein about 0.1 to about 2.5 mole % of R is 4SP, an alkali metal or alkaline earth metal salt of a 4-sulfophthalic radical, up to about 40 mole % of R is a radical D selected from the group consisting of a chemical bond and one or more divalent, non-aromatic, C$_1$–C$_{10}$ hydrocarbylene radicals, and the remainder of R is a divalent aromatic radical, with at least about 85 mole % of said remainder being p-phenylene (T), wherein G is up to about 30 mole % of a polyethylene ether radical E selected from the group consisting of DEG and TEG, —(CH$_2$)$_2$—O—(CH$_2$)$_2$— and
—(CH$_2$)$_2$—O—(CH$_2$)$_2$—O—(CH$_2$)$_2$—, and the remainder of G is selected from the group consisting of a radical F, being a polyalkylene ether of molecular weight at least about 250, and of hydrocarbylene radicals —(CH$_2$)$_2$— (i.e., 2G), —(CH$_2$)$_3$— (i.e., 3G) and —(CH$_2$)$_4$— (i.e., 4G),
and wherein the structural units of the formula:

[—C(O)—R—C(O)—OGO—]$_a$ contain amounts of radicals D and/or E and/or F that are at least S, wherein S is the total of d+e+f, wherein d is the mole % of radical D, e is one quarter of the mole % of radical E, and f is the mole % of radical F, and wherein S is at least 5 mole %,
wherein Q is derived from an hydroxy acid of formula HO[—C(O)—Q—O—]$_x$H, where x is an integer, such hydroxy acid having a melting point at least 5 C below its decomposition temperature, and Q is selected from the group consisting of a chemical bond and hydrocarbylene radicals —(CH$_2$)$_n$—, where n is an integer from 1 to 5, —C(R')H—, and —C(R')HCH$_2$—, wherein R' is selected from the group of —CH$_3$ and —CH$_2$CH$_3$, and wherein "a" and "b" are mole fractions of the polymer, and the mole fraction "a" may be 0.6 to 1 and, correspondingly, mole fraction "b" may be 0 to 0.4.

The acid component preferably includes about 1.5 to 2 mole % 4SP. This component is not only relatively costly but also excessively large amounts can render the polyesters water soluble and thus affect the fiber and film physical properties such as shrinkage. Small amounts of 3-sulfophthalic acid may be present as an impurity in 4SP, especially in commercial material. As little as 0.1 mole % of 4SP contributes significantly to the degradability characteristics of the resultant fibers and films. The metal ion is preferably an alkali metal such as sodium, potassium or lithium. However, alkaline earth metals such as magnesium are also useful. The sodium salt 4-sulfophthalic acid has given very good results.

Up to about 40 mole % of the R radicals, and advantageously, about 5 to 40 mole %, may be an alkylene or other residue from an organic C$_2$–C$_{12}$ non-aromatic dibasic acid. These are referred to as radicals D.

Of the remainder of R, at least about 85 mole % (i.e., about 60 to 95 mole % of R) is preferably T (para-phenylene), with optional inclusion of up to about 15 mole % of I (meta-phenylene). Polyesters in which at least about 97.5 mole % of R is p-phenylene and the remainder is 4SP are also preferred, as being economically attractive.

Of the G radicals, up to about 30 mole %, and advantageously about 20 to 30 mole %, may be DEG and/or TEG (i.e., polyethylene ether radicals —(CH$_2$)$_2$—O—(CH$_2$)$_2$— and —(CH$_2$)$_2$—O—(CH$_2$)$_2$—O—(CH$_2$)$_2$—, respectively). These are referred to as radicals E.

Optionally, if desired, some of the G may be PAG (a radical of a polyalkylene glycol of MW at least about 250). This is referred to as radical F.

The remainder of G may be 2G, 3G and/or 4G (i.e. C$_2$–C$_4$ lower alkylene groups).

Any Q radicals are from an hydroxy acid, as indicated, for example, in application Ser. No. 07/645,995.

The polyesters of the invention are not soluble in water (in contrast to like polyesters derivable from the same constituents but with very much higher mole percentages of 4SP). They also have relatively low glass transition temperatures, Tg.

This is why it is desirable that some of the R be a radical D and/or some of the G be a radical E and/or F. Thus, desirably, at least 5 mole % of the R should be a radical D. Or at least 5 mole % of the G should be PEG or other radical F. However, at least 20 mole % of the G may desirably be a radical E (DEG and/or TEG). Copolyesters having two or more of these types of radicals (D, E and/or F) may also be used. Accordingly, this requirement is indicated as provision of these radicals in amount S, wherein S=d+e+f and is at least 5 "mole %, d[e] and f being, respectively, the mole % amounts of radicals D[E] and F, and e being one quarter of the mole % of radical E. Inclusions of these radicals lower the Tg and melting points, which is". important with regard to compostability, and also ease of inclusion of Q radicals, when desired.

Thus, advantageously the Tg of the polyester articles, such as fibers, foams or films, should be no higher than approximately the temperature at which degradation will take place. Since the temperatures in composting operations are often no higher than about 70 C., it is desired that the Tg of the polyester be no more than about 70 C., preferably about 65 C. or below. Commercial unmodified polyethylene terephthalate (abbreviation 2GT) polyester fibers have a higher Tg of about 80 C. The replacement of some terephthalic acid with an aliphatic acid, such as azelaic, succinic, adipic, sebacic or glutaric acid, is advantageous in lowering the Tg.

Such organic non-aromatic dibasic acid for radical D is preferably adipic and/or glutaric acid, but may be azelaic, succinic, sebacic or other acid, ranging from oxalic acid (C$_2$) to dodecanoic acid (C$_{12}$), as dibasic acids having larger numbers of carbon atoms are not yet commercially available. The more of such acid that is added, the more significant is the effect of such incorporation. It is not, however, desirable to lower the melting point of the polymer to such an extent as to impair its usefulness, depending on the desired end-use, and it is generally desirable to incorporate no more than about 40 mole % of such acid. Preferred amounts are 10-30 mole %.

The polyesters of the invention may be prepared by conventionally polycondensation techniques using, for example, as the glycol component, a combination of about 70 to 80 mole % of ethylene glycol with complementally about 20 to 30 mole % of diethylene glycol, and as the acid component, a combination of about 97.5 to 99.9 mole % of terephthalic acid with about 0.1 to 2.5 mole % of a metal salt of 4-sulfophthalic acid. Optionally as indicated, some of the glycol components or terephthalic acid can be replaced, respectively, by another glycol or by another acid, especially an aliphatic acid. In lieu of the mentioned dicarboxylic acids, ester forming derivatives such as the dimethyl esters of the acids may be used.

It will be understood that with minor variations in composition, it is possible for the polyesters of the invention to have a further significant reduction in their Tg values. For example, the replacement of some of the terephthalic acid with an aliphatic acid such as azelaic, succinic, adipic, sebacic or glutaric acid or the replacement of some of the ethylene glycol with another glycol such as triethylene glycol can lower the Tg even below 65 C.

The glycol component is preferably about 20 to 25 mole % DEG or TEG and about 75-80 mole % 2G, 3G or 4G, to achieve an optimum level of degradability without a major sacrifice to fiber and film physical properties such as tensile strength. Above about 40 mole % DEG such properties are adversely affected while with less than about 20 mole % DEG, the degradability may become inadequate, unless PEG (radical F) or an aliphatic acid (such as for radical D) is used instead or in addition.

A relative viscosity of at least 16, preferably at least about 18, is generally acceptable for melt spinning performance.

Minor amounts of polyfunctional branching agents, such as trimellitic acid residues, may be incorporated to modify melt rheology and film processing, if desired.

In the Examples which follow, the various monomeric components are charged to a polymerization vessel along with an antimony or other catalyst and subjected to polycondensation conditions to produce a linear polyester in which the units are randomly distributed along the molecular chain. It will be understood that it is also possible, however, to first react two or more of the monomeric components to a prepolymer stage followed by addition of the remaining components and completion of the polymerization.

The polyesters of the invention are very hydrolytically sensitive, having a higher equilibrium moisture content than 2G-T resin and a faster moisture regain rate. It is desirable that isolated flake be dried thoroughly, preferably to a moisture content below 400 ppm before reextrusion, and to maintain a nitrogen atmosphere around all possible air in leakage points, and to transfer polymer in warm condition (e.g., above about 50 C.) from the dryer to the extruder.

The polyesters as isolated from the reactor usually have multiple melting points by DSC analysis. These are seen at temperatures which overlap those which might be used in drying 2G-T flake, making it difficult to dry these polymers without fusing the flake into a solid mass when they are rapidly heated to get fast economical drying rates. Slower heating to allow crystallization, after which heating at higher temperatures for fast drying, is desirable.

A desirable procedure for preparing high molecular weight resins from rapidly polymerized lower molecular weight ones may be to use solid phase polymerization of low molecular weight flake. This procedure may desirably be carried out after or in combination with the crystallization procedure mentioned above so that temperatures high enough for rapid polymerization can be attained without fusing of the flaked resin. In addition, as known from U.S. Pat. No. 3,544,523, anticaking agents may be useful to prevent sticking, such as Cab-o-sil grade MS-75D, or other finely divided inert solids, like $TiO_2$, talc, carbon black and clay.

If it is desired, for environmental or other reasons, to avoid use of a catalyst that comprises antimony or another heavy metal, then this may be achieved, for instance, by using a crystalline sodium aluminosilicate molecular sieve such as Linde Molecular Sieve 13X, type 9356, with a nominal pore size of 10 Å, obtained from Union Carbide Corporation. Such procedure is more fully described in commonly assigned U.S. application Ser. No. 07/497,069 filed Mar. 20, 1990 in the name of Jackson, but other methods of avoiding antimony may be used, if desired.

In any event, the particular mole percentages of the aforementioned components are desirably selected to provide a polyester which in fiber or film form has a Tg of 70 C. or less, preferably of about 65 C. or less.

As will be understood, while the polyesters of the invention are well suited for use as fibers or filaments in nonwoven sheets, they can be used to particular advantage in the form of cast and blown films, foams, coatings, laminates, molded articles, or wherever polyesters with such properties are desired.

An important aspect of the invention is, however, the production of fibers or filaments from the above-described polyesters. Fibers and filaments herein are interchangeable terms in the general sense, but where a more specific acknowledgement of length is appropriate, the term "fibers" is intended to refer to short filaments as in "staple fibers". Hereafter only one of the terms may be used.

The polyesters of the invention may be converted to fibers or filaments by conventional melt spinning techniques. Deniers of 2 to 15 dpf are most common. The filaments may be used as-spun(undrawn) or in a stretched (drawn or oriented) condition. Drawing to reduce denier or for increasing orientation can be accomplished by the usual procedures.

The polymer compositions of the invention can be formed into nonwoven fabrics via a number of processes. These may be roughly divided into spunbonded fabrics and those fabrics using staple fibers. These are discussed in "Encyclopedia of Textiles, Fibers and Nonwoven Fabrics", Ed. Martin Grayson, John Wiley and Sons, New York, 1984, pp 252-304. The compositions described herein can be used in many such products. Spunbonded nonwovens can be prepared by spinning and laying down simultaneously into webs of continuous filaments using known methods of distributing the threadline in the desired orientation in the web plane. Such webs can be thermally bonded under suitable conditions of time, temperature and pressure to strong fabrics with tensile properties which are usually superior to those obtained with staple webs. Bonding can also be carried out by using suitable adhesives and both these methods may be used to make point bonded or area bonded fabrics. Needle punching may also be used to give the webs stability and strength. Spunbonded fabrics can also be made by melt blowing wherein a stream of molten polymer is extruded into a high velocity stream of heated air and a bonded web formed directly on a screen conveyor from the resultant fibers. Nonwoven fabrics can also be made by direct extrusion through a rotating die into a netlike product (U.S. Pat. No. 3,959,057 J. J. Smith) or by stretching and drawing embossed films of the thermoplastic polymers (British Patent 914,489 and 1,548,865 to Smith and Nephew Research Ltd.).

Staple fibers can be made into nonwovens by several processes. Most of these can be classified into (1) web preparation and (2) reinforcing ("Manual of Nonwovens", Dr. Radko Krcma, Textile Trade Press, Manchester, England, pp 74–76, 1971). During web preparation, bales of staple fiber are opened and formed into a web having either a random orientation (via air, water or electrostatic deposition) or parallel or crosslaid orientation (via carding and plying). Reinforcement to impart physical integrity and useful mechanical properties can be accomplished by mechanical means such as needlepunching or hydroentanglement (where water jets move fibers out of the plane of the web and entangle them) as in the spunlaced fabrics (U.S. Pat. No. 3,485,706 to Du Pont) or by stitchbonding where a reinforcing thread is sewn through the web. (See "Principles of Stitch Through Technology" Nonwovens Fabrics Forum, Clemson University, Clemson, S.C. 1978 by J. D. Singelyn). Reinforcement can also be accomplished by adhesive bonding which includes impregnation of the web by a water based resin binder solution or dispersion and subsequent evaporation of the water leaving a fabric which is composed typically of 60–70% by weight fiber and 30–40% by weight binder. Dry adhesive powders may also be applied to the staple web prior to a heating step to produce a powder-bonded nonwoven. Webs of thermoplastic staple fibers may also be reinforced by thermal bonding in which use is made of the ability of the fibers to soften and adhere to each other upon application of heat. As with the spunbonded fabrics these may be point bonded or area bonded. Heat may be applied by hot air (known as through air bonding) or by a pair of patterned and/or flat heated rollers which form a nip through which the web passes to achieve bonding. This process may be carried out with 100% thermoplastic fibers or with blends of thermoplastic fibers with fibers which do not thermally bond in the 100% form, i.e., cotton and rayon.

In addition, useful articles can also be made by laminating, extrusion melt coating or adhesively combining the above types of nonwoven fabrics with each other, with films or with staple webs in such a way as to confer desired properties on the combined fabric.

In particular, a fabric made by extrusion melt coating a thin, pinhole-free film of the compositions of this invention on a nonwoven, made by the spunbonded process or by thermally bonding staple from fibers of this invention alone or in combination with other compostable fibers such as cotton or rayon, is aesthetically pleasing and non-fluid permeable.

The compostable polyester fibers described herein may be used in all these methods of preparing nonwovens to yield fabrics which when subjected to composting conditions will be substantially degraded. Thus staple webs of the polyester fibers, as well as blends of these fibers with cotton and rayon, may be bonded by hydro entanglement, by needle punching, by wet resin bonding and by dry adhesive bonding. (The adhesives used should be chosen to allow the desired degradation under composting conditions.)

Thermally bonded staple webs of the described compostable polyester fibers can be made in the 100% form or webs containing a significant proportion of these fibers together with cotton and/or rayon may be thermally bonded to fabrics having useful mechanical properties.

Continuous or spun yarns prepared from the compositions described herein may be used to stitch bond webs of fibers such as cotton, rayon or blends of these fibers, or wood pulp, with the compostable polyester fibers of this invention resulting in fabrics which will degrade under composting conditions.

Spunbonded fabrics can be made by thermally bonding webs of continuous fibers prepared from the compostable polyester compositions described herein, and by blow spinning, direct extrusion to nets and drawing of embossed films.

The compostable compositions described herein can be melt extruded as films to coat spunlaced nonwoven fabrics which themselves may be composed of compostable fibers alone or in combination with wood pulp, rayon or cotton.

A process for preparing ultramicrocellular and plexifilamentary products is disclosed in U.S. Pat. No. 3,227,784 (Blades et al) and durable plexifilamentary and microcellular products are described in U.S. Pat. No. 3,227,664 (Blades et al) and U.S. Pat. No. 3,081,519 (Blades et al).

Extrusion of foamed plastics has also been described, for example in Modern Plastics Encyclopedia October 1990 Vol 67 #11 pp 291-2. In foam extrusion, molten polymer is first mixed with a relatively small amount (e.g. 1 to 15 wgt %) of a blowing agent. The blowing agent used does not have to be a true solvent for the polymer. When the mixture is extruded, the blowing agents expand due to depressurization and/or volatilization to form a microcellular structure. Unlike in flash spinning, most of the blowing agents used do not leave but stay inside the foam. Most commonly used blowing agents are:1). gaseous materials such as nitrogen and carbon dioxide, 2). low boiling organic solvents such as hydrofluorocarbons (e.g. HFC-134a, 152a, 125), hydrochlorofluorocarbons (e.g. HCFC-22, 123, 141b, 142b, 124), and hydrocarbons (e.g. isobutane, pentane). In addition to these types of physical blowing agents, chemical blowing agents are also used to make foams. Chemical blowing agents decompose at elevated temperatures or through chemical reaction to generate gases. Nucleating agents which are finely divided powders such as fumed silica are usually added to encourage the formation of small uniform cells.

Nonwoven webs of the compostable compositions made by the melt blowing process may also be used as an adhesive layer between other nonwoven fabrics.

It is apparent that the fiber, film, foam, and sheet products made from compositions described herein have a great number of applications in products which are disposed of or potentially may be disposed of in composting systems. In addition the compositions have utility in objects made by injection molding, injection blow molding, thermal forming of sheets, rotational molding of powder, extrusion, and pultrusion, which desirably can be disposed of and degraded in composting systems. The following is a nonexclusive list of such end uses:

- Agricultural mulch
- Agricultural mats containing seeds
- Nutrients
- Adhesive tape substrate
- Baby pants
- Bags
- Bag closures
- Bed sheets
- Bottles
- Cartons
- Disposable diapers
- Dust bags
- Fabric softener sheets
- Garment bags
- Garbage and lawn waste bags
- Industrial bags
- Labels, tags
- Monofilaments
- Packaging materials and structures
- Pillow cases
- Protective clothing
- Surgical drapes
- Surgical gowns
- Surgical sheets
- Surgical sponges
- Tampon applicators
- Temporary enclosures
- Temporary siding
- Toys
- Wipes.

The invention can provide fluid impermeable sheets which are compostable in typical waste disposal facilities. Preferably these sheets should not rattle or rustle objectionably and should have strength and toughness adequate for use in personal absorbent products, such as disposable diapers.

The fibers, films, foams and nonwoven fabrics prepared from the compositions of the present invention are of particular utility in disposable diapers since in that use they have an enhanced capability of being degraded in a composting operation. Typical examples of disposable diaper constructions are given in U.S. Pat. Nos. 3,860,003 (Buell) and 4,687,477 (Suzuki et al.), the disclosures of which are incorporated herein by reference. Items which can be made of the compostable compositions of this invention include:

(1) the backsheet film, i.e., the water-impermeable outside layer, which may be a film which is 100% of the compostable composition or it may be a laminated sheet with a nonwoven or web of compostable fibers including cotton or rayon adhered to the film, or it may be a film adhered to a suitable grade of paper, (2) the topsheet, i.e., the water permeable or inner layer, which is a film of a composition of the invention or a nonwoven fabric of the compostable fiber composition or a blend of the compostable fiber of this invention with cotton or rayon fiber, having a porosity suitable for passing urine quickly to the fluid absorbing pad between the topsheet and backsheet, (3) the fastening tapes which may optionally be made from films or nonwovens of the compositions of the invention; the fastening tapes are typically coated with a pressure sensitive adhesive, (4) the frontal landing strip, which may be made from films of this invention; the frontal landing strip is typically printed with a decorative design and coated with a pressure sensitive adhesive, (5) the flexible foam optionally inserted into the diaper under modest extension to gather the waist, leg openings, and/or barrier leg cuffs may be made from polymers of this invention, (6) hot melt adhesives used to bond the diaper components to one another may be formulated to incorporate polymers of this invention, (7) the leakage shield used at the diaper waist, in front and back, may be made from films of this invention, and may be glued, thermally bonded, or sonically bonded to the topsheet or the topsheet and backsheet, (8) additives to the absorbent cellulose pulp core, which may be short fibers, fibrids, synthetic pulp prepared by flash spinning, or some other mechanically dispersable and finely divided form made from polymers or fibers of this invention, and which serve to increase wet strength of the core, particularly when superabsorbent polymers have been incorporated and pulp content subsequently reduced, (9) other minor components of the diaper which require the combination of compostability and thermoplastic fabrication and/or processing, and

(10) diaper packaging, which may comprise a bag made of film of compositions of this invention, or paper or cardboard coated with film of compositions of this invention.

It will be apparent that the products of the invention may contain additives such as dyes, fillers, pigments, plasticizers, etc. Indeed, use of appropriate fillers or other additives may be helpful, as an acceptable way to enhance disintegratability. Use of starch is particularly helpful, as taught in Application (QP-4850). The incorporation of finely divided particulates has likewise been found helpful, for instance incorporating similar amounts of calcium carbonate in similar compositions. As the incorporation of large amounts of such a filler may increase the tendency of articles to embrittle to an extent that could be undesirable for certain end uses, it may be desirable to take steps such as adding a plasticizer to counter such tendency. Indeed, the addition of materials such as low molecular weight polyethylene adipate (Rucoflex Mn=2000) to particulate blends has been found to provide further advantage in accelerating disintegration of related compositions under composting conditions. Also, in regard to such filled articles, microporous films are taught by Moss in U.S. Pat. No. 4,698,372, and similar techniques may be followed with products of the present invention. Advantageous results have been obtained by using blends of related compositions with tartarates and citrates, such as dibutyl tartarate and triethyl citrate. The addition of low molecular weight polyethylene adipate (Rucoflex Mn=2000) has also been shown to reduce rattle or rustle of films of related polymers. So incorporation of appropriate additives would be expected to be advantageous for the polymers of the present invention.

TEST METHODS

Polyester glass transition temperatures, Tg, are obtained by using a Du Pont model 2910 Differential Scanning Calorimeter. Samples are heated under a nitrogen atmosphere at a rate of 20 C./min. to a temperature 10-20 C. above the melting point, then the melt is cooled using the rapid air quench capability of the instrument. The Tg is determined from the second cycle scan done at 20 C./min. using the internal software to determine the inflection point of the baseline shift.

Polymer melting point, m.p., is determined on the first heating cycle as described in Tg determination. The temperature at which the highest endothermic peak occurs is reported as the polymer melting point.

Number average molecular weight, Mn, is determined by gel permeation chromatography (gpc) versus a standard polyethylene terephthalate sample with an Mn of 22000 and a weight average molecular weight of 44000. Polymers are dissolved in and the analysis is run using HFIP (hexafluoroisopropanol) containing 0.01M sodium trifluoroacetate as the solvent. A Waters model 150 CALC/GPC instrument, or its equivalent, is used with two Zorbax PSM-S biomodal columns (sold by E. I. du Pont de Nemours and Company) (or equivalent) in series at 30 C. A refractive index detector was used and data collected at 100 intervals and analyzed via software provided by the instrument supplier.

Carboxyl end groups are determined by titration of an o-cresol solution of the polymer at 115 C. with KOH in benzyl alcohol to a colorimetric endpoint using bromophenol blue as the indicator. Results are reported in eq./$10^6$ grams of polymer.

Inherent viscosity is defined in "Preparative Methods of Polymer Chemistry", W. R. Sorenson and T. W. Campbell, 1961, p. 35. It is determined at a concentration of 0.5 g/100 ml of the indicated solvent at the indicated temperature, usually HFIP at 30 C.

Tensile Properties of fibers and yarns are sometimes coded as T/E/M/To for tenacity, elongation, initial modulus, and toughness and are reported in their conventional units of grams per denier, percent, grams per denier, and grams per denier. These are measured on conditioned (65% RH, 70 F.) samples (3 inch gauge length) in a commercial testing machine at the rate of extension of 50% per minute (unless otherwise indicated). Toughness (To) is measured as the integrated area under the stress-strain curve.

Relative viscosity is the ratio of the viscosity of a solution of 0.8 gram of polyester dissolved in 10 ml of hexafluoroisopropanol (HFIP) containing 80 ppm $H_2SO_4$ to the viscosity of $H_2SO_4$-containing HFIP itself, both measured at 25 C. in a capillary viscometer and expressed in the same units.

Crimp index is measured by straightening a crimped tow by application of about 0.1 gpd load. Then 0.5 gm clips 66.6 cm apart are attached to the extended tow. The tow is then cut 11.2 cm beyond each clip to give a sample of 90 cm extended length. The sample is suspended vertically, hanging freely from one of the clips to allow retraction to crimped length. After about 30 secs., clip to clip distance is measured.

$$\text{Crimp Index} = \frac{(66.6 - Lc)}{66.6} \times 100$$

where Lc is the clip-to-clip distance in the free-hanging state.

Crystallinity index is measured by first obtaining a diffractogram as described by Blades (U.S. Pat. No. 3,869,429, col. 12) with some modifications. The high intensity X-ray source is a Phillips XRG-3100 with a long fine focus copper tube. Diffraction is analyzed with a Phillips single axis goniometer equipped with a thetacompensating slit and a quartz monochromator set to exclude copper $K_b$ radiation. Diffracted radiation is collected in step scanning mode in 0.025 steps with a 1.5 sec. per step count time. The digital data so collected are analyzed by a computer and smoothed by a running fit to second order polynomial. The computer is programmed to define a straight base line which joins the diffractogram tangentially at about 113 and 343. Crystallinity index is defined as $$\frac{A \times 100}{A - B}$$

where A is the intensity of the 18 010 peak above this base line and B is the intensity of the 20 minimum above this base line. Crystallinity index has been related to percent crystallinity determined by density (see U.S. Pat. No. 4,704,329, col. 8,9). Weight percent crystallinity = 0.676 X Crystallinity index.

The invention will be further illustrated by the following Examples wherein, unless otherwise indicated, parts and percentages are by weight and the polymer compositions are mole %, using the same abbreviations. The "Hydrolysis" results are generally after boiling in water at 100 C, as indicated, and generally show reductions in tenacity, and/or molecular weight (Mn), as percentages.

EXAMPLE 1

This Example describes the preparation of the dimethyl ester of 4-sulfophthalic acid (4SP), its polymerization in a copolymer of the composition 2G/DEG(80/20)-T/4SP(98/2), spinning this polymer to fibers and evaluation of the hydrolysis rate of this fiber vs. a control fiber without 4SP)

50 g of a 50% solution in water of 4-sulfophthalic acid (Aldrich Chemical Co, containing some 3-sulfophthalic acid) was distilled to remove most of the water at a pressure of 0.3 mm Hg. Then a mixture of 200 ml methanol and 35 ml toluene were added and distillation carried out at atmospheric pressure over about 5 hours. Addition of the same mixture followed by distillation was repeated a total of 3 times leaving about 150 ml of solution. 20 g of anhydrous sodium acetate were added, resulting in precipitation of a white solid. Filtration of the solid and evaporation of about ⅓ of the filtrate gave more white precipitate. These products were then recrystallized (from water or methanol before use.).

In a reaction kettle fitted with a distillation head, a $N_2$ inlet and a stirrer were placed:

83.7 g glycol (2G)
15.9 g diethylene glycol (DEG)
0.143 g $Sb_2O_3$
0.115 g $Mn(OAc)_2.4H_2O$ This was heated to 160 C with stirring to dissolve the catalysts and the following were added:

143.3 g of dimethyl terephthalate (DMT)
3.55 g sodium dimethyl 4-sulfophthalate (4SP)

This mixture was heated slowly to 220 C (bath temperature) and methanol distillate was collected. The molten prepolymer was then transferred to a polymer tube with a side arm a finely drawn capillary $N_2$ tube inserted with the tip near the bottom of the tube. The polymer tube was immersed in a dimethyl phthalate vapor bath and polymerization was carried out by removing glycol vapor first at laboratory vacuum for 1 hour then at 0.3 mm Hg pressure for 2.5 hours.

The polymer was molded into a ⅝ inch diameter plug and spun from an electrically heated vessel in a press-spinning apparatus through 3 holes 0.009 inch diameter ×0.027 inches long, at a temperature of 245 C, a delivery rate of 0.7 cc/min., and a windup speed of 27 m/min. These fibers were drawn 5.5X over a 100 C hot pin. T/E/M/To=2.5/36/46.5/0.65 (gpd/%/gpd/gpd/gpd/gpd) (19 dpf) when tested on an Instron at 3 inch gage length and an elongation rate of 50%/min.

Hydrolysis was carried out by boiling a sample of the fiber in deionized water, removing samples at the indicated times and determining Mn via gpc. Initial Mn=24530. After 8 hrs, Mn=23090. After 24 hrs, Mn=17100 (30% reduction in Mn).

A fiber with the composition 2G/DEG (76/24)-T made in a similar way (without any 4SP) had an initial Mn=33200 and after 24 hrs in boiling water Mn=30400 (i.e., only an 8% reduction in Mn)

EXAMPLE 2

This shows the preparation of a copolymer 2G-T/6/4SP(78.4/20/1.6), preparation of fibers, and hydrolysis of the fibers.

The copolymer was made by the following procedure:

In a 500 ml reaction kettle fitted with a distillation head, a $N_2$ inlet and a stirrer were placed:
- 93.0 g ethylene glycol (2G)
- 1.0 ml 10% tetrabutyl titanate in glycol solution This was heated to 160 C with stirring and the following added:
- 114.2 g of dimethyl terephthalate (DMT)
- 26.1 g dimethyl adipate (6)
- 3.6 g sodium dimethyl 4-sulfophthalate (4SP)

This mixture was heated slowly to 220 C (bath temperature) and methanol distillate was collected. The molten prepolymer was then transferred to a polymer tube with a side arm and a finely drawn capillary $N_2$ inlet tube was inserted with its tip near the bottom of the tube. The polymer tube was immersed in a diphenyl ether vapor bath and polymerization was carried out by removing glycol vapor, first at laboratory vacuum for 1.5 hours, then at 0.3 mm Hg pressure for 4 hours. The polymer had a reddish color.

Fiber spinning was carried out as follows. The ground polymer was dried overnight under laboratory vacuum at about 90 C., then molded into a ⅜ inch diameter plug, which was placed in a press spinning apparatus and spun through a 5 hole spinneret with 0.015 inch dia×0.045 inch long holes, at a spinneret temperature of 204–220 C. at a delivery of about 0.7 cc/min, taken up on a roll running at 40 m/min. and drawn 2X over a hot pin at 80 C. Fiber properties were T/E/M/To=0.5/317/11/0.92. Hydrolysis was carried out at 60 C. in water in a capped Erlenmeyer flask shaken in an air thermostat. The Mn was initially 20650. After 3 days it was 5480, i.e., a 73% reduction.

In comparison, a film with the composition 2G-/6(75/25) (no 4SP) having an initial Mn of 38600 was hydrolyzed in boiling water (100 C.). The Mn after 8 hours was 38000 (2% reduction). After 24 hours it was 34200 (11% reduction).

EXAMPLE 3

The biodegradability of the ultimate product from hydrolysis of the sulfonated dicarboxylic acid monomer sodium 4-sulfophthalic acid (4SP) was determined by a $CO_2$ Production Test designed to determine the rate and extent of conversion of the carbon content of the test material to $CO_2$ by the microorganisms in an activated sludge acclimated by prior exposure to the test substance.

The test was carried out on 2 liters of combined test medium, test substance, and inoculum in 4 L Erlenmeyer flasks shaken at 110 rpm in a temperature range of 21.8–23.5 C. The test medium was water containing 1 ml 2.25% magnesium sulfate solution, 1 ml 2.75% calcium chloride solution, 2 ml pH 7.2 phosphate buffer solution (Fisher SP341-1), 4 ml 0.025% ferric chloride solution and 1 ml 4% ammonium sulfate solution per liter. The acclimated inoculum was prepared in individual semicontinuous activated sludge (SCAS) units using activated sludge from the Avondale Sewage Sludge Treatment Plant, Avondale, Pa. The solids were adjusted to 2500 mg/L and the test substance gradually increased to 40 mg/L concentration. The units were maintained at 40 mg/L while being fed synthetic sewage daily until the sludges were used as a source of innoculum for the $CO_2$ generation study. The innoculum was prepared by homogenizing 400 ml of liquor from the SCAS unit in a blender for 2 min, settling for 30 min. and decanting. 20 ml of inoculum was added to each test flask. The $CO_2$ generation rate was determined by titration of attached traps containing $Ba(OH)_2$ solution at 2 day intervals for 4 days and then at 3 day intervals to a total of 28 days. Two concentrations of test substance (20 and 40 mg/L) were run for each substance, i.e., for 4SP and for the dimethyl ester of 5SI, as well as an active control (d-glucose, 20 mg/L) and a blank. Results are given in the Table:

TABLE

| Substance | Conc mg/L | Period Days | % Theo $CO_2$ |
|---|---|---|---|
| 4SP | 20 | 28 | 73.3 |
| 5SI | 20 | 24 | 6.7 |
| 4SP | 40 | 28 | 72.1 |
| 5SI | 40 | 24 | 2.6 |
| d-glucose | 20 | 28 | 76.2 |
| Blank | | 28 | —<0.5 |

The ratio of carbon incorporated in biomass to carbon released as $CO_2$ will vary depending on the organic substrate, experimental conditions and the microorganisms metabolizing the substance. Generally the amount of $CO_2$ produced will not be 100% of the total amount possible, even though 100% of the carbon initially added may be metabolized. The near equivalence of theoretical $CO_2$ generated for 4SP and glucose during the 28 day period is taken as indicating substantially complete biodegradation of 4SP.

What is claimed is:

1. A fiber and film forming polyester consisting essentially of recurring structural units of the formulae:

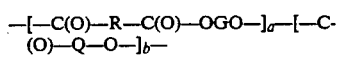

wherein about 0.1 to about 2.5 mole % of R is an alkali metal or alkaline earth metal salt of a 4-sulfophthalic radical, up to about 40 mole % of R is a radical D, in amount d, selected from the group consisting of a chemical bond and one or more divalent, non-aromatic, $C_1$-$C_{10}$ hydrocarbylene radicals, and the remainder of R is a divalent aromatic radical, with at least about 85 mole % of said remainder being p-phenylene, wherein up to about 30 mole % of G is a polyethylene ether radical E, in amount 4e, selected from the group consisting of —(CH$_2$)$_2$—O—(CH$_2$)$_2$— and
—(CH$_2$)$_2$—O—(CH$_2$)$_2$—O—(CH$_2$)$_2$—, and the remainder of G is selected from the group consisting of hydrocarbylene radicals —(CH$_2$)$_2$—, —(CH$_2$)$_3$—, and —(CH$_2$)$_4$—, and wherein the structural units of the formula:

[—C(O)—R—C(O)—OGO—]$_a$ contain a total amount of radicals D and/or E that is at least S, wherein S is the total of d+e, where d is the mole % of radical D and e is one quarter of the mole % of radical E, and wherein S is at least 5 mole %,
wherein Q is derived from an hydroxy acid of formula HO[—C(O)—Q—O—]$_x$H, where Q is selected from the group consisting of a chemical bond and hydrocarbylene radicals —(CH$_2$)$_n$— (where n is an integer from 1 to 5), —C(R')H—, and —C(R')HCH$_2$—, wherein R' is selected from the group of —CH$_3$ and —CH$_2$CH$_3$, and where x and Q are selected such that the hydroxy acid has a melting point at least 5 degrees C below its decomposition temperature,
and wherein "a" and "b" are mole fractions of the polymer, and the mole fraction "a" is 0.6 to 1 and, correspondingly, mole fraction "b" is 0 to 0.4.

2. A fiber and film forming polyester consisting essentially of recurring structural units of the formulae:

—[—C(O)—R—C(O)—OGO—]$_a$—[—C(O)—Q—O—]$_b$— wherein about 0.1 to about 2.5 mole % of R is an alkali metal or alkaline earth metal salt of a 4-sulfophthalic radical, up to about 40 mole % of R is a radical D selected from the group consisting of a chemical bond and one or more divalent, non-aromatic, C$_1$-C$_{10}$ hydrocarbylene radicals, and the remainder of R is a divalent aromatic radical, with at least about 85 mole % of said remainder being p-phenylene,
wherein up to about 30 mole % of G is a polyethylene ether radical E selected from the group consisting of —(CH$_2$)$_2$—O—(CH$_2$)$_2$— and —(CH$_2$)$_2$—O—(CH$_2$)$_2$—O—(CH$_2$)$_2$—, and the remainder of G is selected from the group consisting of a polyalkylene ether radical F of number average molecular weight at least about 250, and hydrocarbylene radicals —(CH$_2$)$_2$—, —(CH$_2$)$_3$—, and —(CH$_2$)$_4$—,
and wherein the structural units of the formula:

[—C(O)—R—C(O)—OGO—]$_a$ contain at least 5 mole % of radical F,
wherein Q is derived from an hydroxy acid of formula HO[—C(O)—Q—O—]$_x$H, where Q is selected from the group consisting of a chemical bond and hydrocarbylene radicals —(CH$_2$)$_n$— (where n is an integer from 1 to 5), —C(R')H—, and —C(R')HCH$_2$—, wherein R' is selected from the group of —CH$_3$ and —CH$_2$CH$_3$, and where x and Q are selected such that the hydroxy acid has a melting point at least 5 degrees C below its decomposition temperature,
and wherein "a" and "b" are mole fractions of the polymer, and the mole fraction "a" is 0.6 to 1 and, correspondingly, mole fraction "b" is 0 to 0.4.

3. A polyester according to claim 1, wherein at least about 97.5 mole % of R is p-phenylene.
4. A fiber of the polyester of claim 1 or 3.
5. A non-woven sheet of the polyester of claim 1 or 3.
6. A film of the polyester of claim 1 or 3.
7. A foam of the polyester of claim 1 or 3.
8. A composite of the film of claim 6 and of a layer of nonwoven sheet or of paper.
9. A disposable diaper which includes an absorbent body portion having on one surface thereof a water permeable sheet of the polyester of claim 1 or 3.
10. A disposable diaper which includes an absorbent body portion having on one surface thereof a water impermeable sheet of the polyester of claim 1 or 3.
11. A polyester according to claim 2, wherein at least about 97.5 mole % of R is p-phenylene.
12. A fiber of the polyester of claim 2 or 11.
13. A non-woven sheet of the polyester of claim 2 or 11.
14. A film of the polyester of claim 2 or 11.
15. A foam of the polyester of claim 2 or 11.
16. A composite of the film of claim 14 and of a layer of nonwoven sheet or of paper.

* * * * *